US00PP09901P

United States Patent [19]

Osiecki

[11] Patent Number: Plant 9,901

[45] Date of Patent: May 20, 1997

[54] SPATHIPHYLLUM PLANT 'S9'

[75] Inventor: Marian W. Osiecki, Marianna, Fla.

[73] Assignee: Oglesby Plant Laboratories, Inc., Altha, Fla.

[21] Appl. No.: 594,689

[22] Filed: Jan. 31, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Rothwell, Figg, Ernst & Kurz, pc

[57] ABSTRACT

A new and distinct cultivar of Spathiphyllum is provided. The plant is small, compact, suitable for production in 10–15 cm pots from a single tissue cultured microcutting; displays good proportion between inflorescence and foliage; maintains symmetrical growth habit at close pot spacing; has vigorous growth; early and abundant branching; exceptionally early, abundant and year-round naural flowering and inflorescences of good quality, with very little green coloration of spathes, from the onset of flowering.

2 Drawing Sheets

SUMMARY OF THE INVENTION

This invention relates to a new and distinct Spathiphyllum cultivar characterized by the following combination of repeatedly observed traits:

1. Small size,
2. compact growth habit,
3. vigorous growth,
4. early and abundant branching,
5. exceptionally early, abundant and year-round natural flowering,
6. good quality inforescence from the onset of flowering,
7. very little green coloration on spathes,
8. good proportion between inflorescence and foliage to 10–15 cm pots,
9. symmetrical growth habit at close pot spacing, and primarily selected for those characteristics being so selected from the progeny of the cross stated below in a cultivated area near Altha, Fla.

ORIGIN AND ASEXUAL REPRODUCTION

The new cultivar is a product of a planned breeding program carried out at Olgesby Plant Laboratories, Inc. near Altha, Fla. The female parent was a selected clone of Spathiphyllum 'Petite' and the male parent was a Spanthiphyllum seedling designated 90 WS 16, characterized by good branching and flowering. The cross was made in 1991, the plant was selected in 1992 and it has been reproduced by tissue culture in the vicinity of Altha, Fla., since 1993 with the characteristics stated, found to be maintained through successive generations.

Parentage of 'S9'

Spathiphyllum 'White Sails'×Spathiphyllum 'Viscount'=Spathiphyllum 90 WS 16

Spathiphyllum 'Petite'×Spathiphyllum 90 WS 16=Spathiphyllum 'S9'

The new cultivar has been identified as Spathiphyllum 'S9'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'S9' was approximately 17 months from planting a single tissue culture produced microcutting and was grown in 15 cm pot.

In the photographs:

DETAILED DESCRIPTION OF THE NEW CULTIVAR

Figure 1:
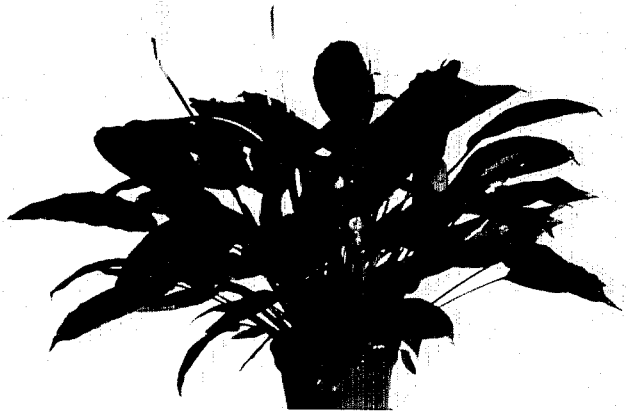
FIG. 1 depicts the whole plant.
Figure 2:
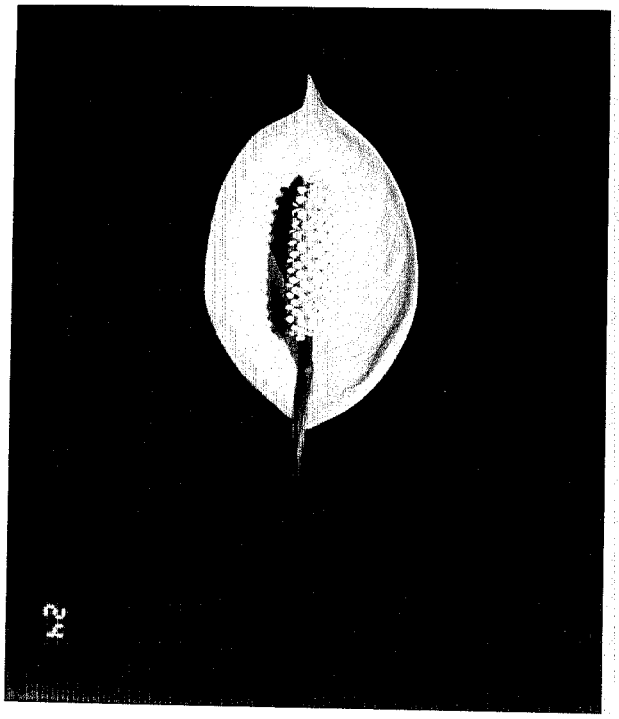
FIG. 2 illustrates the mature inflorescence.
Figure 3:
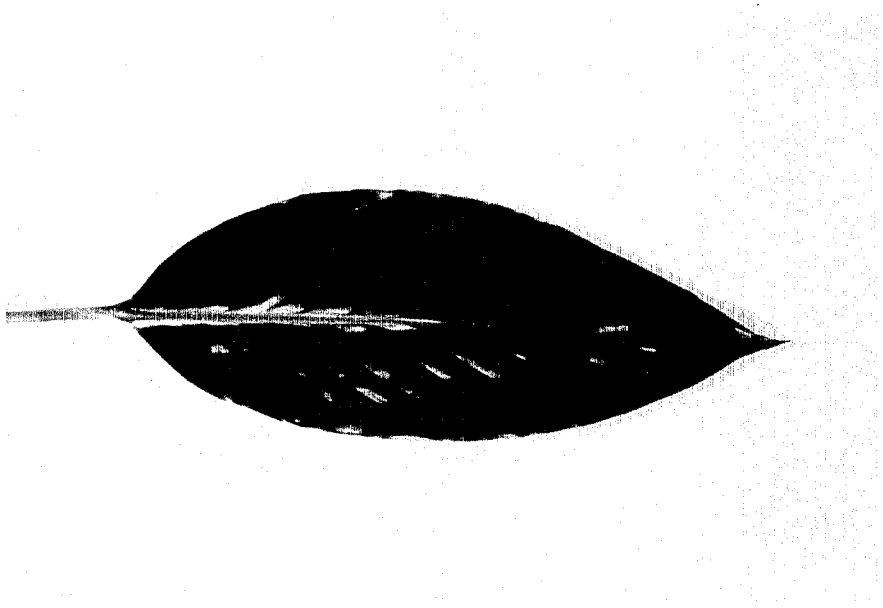
FIG. 3 illustrates the top of a mature leaf.
Figure 4:
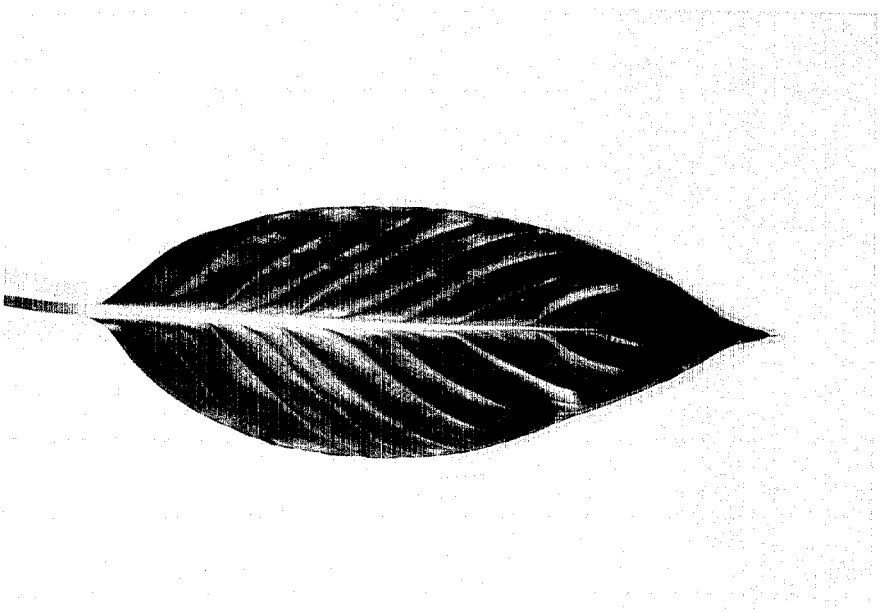
FIG. 4 illustrates the bottom of a mature leaf.

The following observations and measurements describe plants grown near Altha, Fla. under greenhouse condtitions. These observations and measurements were recorded in November and December, 1994 from mature plants (about 13 months from planting microcuttings) grown in 15 cm pots. Fully developed organs were used for measurements. Color values were determined on Nov. 11, 1994, under natural, indirect light of 200–250 foot-candles. Color references are made to The R.H.S. Color Chart, except where general color terms of ordinary significance are used.

'S9' has not been observed under all possible environmental conditions. The phenotype may vary with variations in environment and horticultural practices, such as temperature, light intensity, day length, fertilization etc., without any change in genotype.

Parentage:

*Female parent.*—Spathiphyllum 'Petite'.

*Male parent.*—Spathiphyllum seedling 90 WS 16.

Propagation: Plant tissue culture.

Plant:

*Growth habit.*—Small size, full, very well branched, relatively wide.

*Height.*—Foliage 33–40 cm, with spathes 46–60 cm.

*Maximum width.*—51–63 cm.

Petiole:

*Size.*—14.8–18.3 cm long, 3.0–4.0 mm in diameter (below geniculum).

*Geniculum.*—2.1–3.0 cm long, 4.0–5.0 mm in diameter.

Leaf blade:

*Shape.*—Elliptic, with lanceolate tendencies, usually slightly asymmetric; tip acuminate, usually bending downwards, sometimes also slightly curled; base cuneate to almost obtuse, narrowly decurrent on peduncle; margin slightly wavy.

*Size.*—18.7–21.5 cm long by 7.8–9.0 cm wide; length: width ratio 2.3–2.5:1.

*Texture.*—Smooth, glossy; young leaves highly polished.

*Veins.*—Well defined and sunken.

*Color.*—Mature leaf: Adaxial: similar to, but usually a little lighter than 147A (yellow - green) and much darker than 137A (green). Abaxial: 147B (yellow - green). Newly unfolded leaf: Adaxial: a little darker than 137C (green), but much lighter than 137B (green). Abaxial: similar or a little lighter than 147B (yellow - green).

Inflorescence:

*Arrangement.*—Spathes carried relatively close to the foliage on strong, straight peduncles. Some peduncles on side shoots are weaker and occasionally may slightly bend. Spadix large in relation to spathe (spathe length: spadix length ratio 1.8–2.4:1) and situated relatively high on the spathe. In a newly opened inflorescence the spadix, spathe edges and peduncle are approximately in the same plane or sometimes spadix leans slightly forward. As the inflorescence matures spadix maintains an upright position and spathe often leans backward from the juncture with stipe. At the time of pollen release spathe edges often form an angle of approximate 25°–35° with the stipe. Rarely a senescing spathe is in a horizontal position.

*Scent.*—Strong scent in the morning hours.

Peduncle:

*Size.*—35–46 cm long (including stipe); the zone 3.5 to 4.5 cm immediately below the spathe 3.0–4.0 mm in diameter, then abruptly narrowing by approximately 0.5 mm; at the abrupt transition peduncle may slightly bend toward the plant axis before spathe opens; some peduncles on the side shoots tend to be thinner than those on the main shoot.

*Color.*—Front: similar to 143A (green) with some addition of 144A (yellow - green) and/or 138A, 137C (green). Back: 144A (yellow - green) with 143A and/or some of 137C, 138A (green).

*Stipe.*—0.8–1.4 cm long (back side), 3.0–4.0 mm in diameter.

Spathe:

*Shape.*—Cupped; elliptic to ovate; tip — between acuminate and cuspidate, slightly curled base — cuneate to obtuse, decurrent, often slightly asymmetric.

*Size.*—7.2–9.3 cm long by 4.7–5.5 cm wide and 1.5–2.0 cm deep; length: width ratio 1.5–1.7:1.

*Color.*—155B (white); green coloration is limited to the midrib and the tip (4–5 mm); front side — the upper ½ of the midrib — slightly green; back side — entire midrib yellow - green (144A); tip predominantly green on both sides.

Spadix:

*Size.*—4.3–4.9 cm long; 1.4 cm–1.6 cm in diameter.

*Color.*—158 A-B (yellow - white).

Botanical flower:

*Perianth.*—Inconspicuous, segments united.

*Pistil.*—Relatively thick, acute, extrudes 2–3 mm beyond perianth, stigma minute.

*Stamens.*—Not visible before pollen release.

Flowering: Flowers naturally in 10 cm pots, about 7–9 months from planting tissue culture produced microcuttings. Continuous year-round flowering. Two to six white spathes constantly present above foliage.

Spathe longevity: Spathe remains white for about 4 weeks following emergence of bud above foliage and then gradually changes to a green color.

Roots: Numerous, thick, fleshy, white main roots, lateral roots not very abundant.

Disease and insect resistance: No unusual susceptibility to diseases or insects noted to date.

COMPARISON WITH THE KNOWN CULTIVARS

The new cultivar can be compared to the known cultivars: 'Petite' and 'Bond A' U.S. Pat. No. P.P. 8,849 (a/k/a Symphony). Observations for comparisions were made on plants grown under similar conditions in a greenhouse near Altha, Fla.

'S9' distinguished from both cultivars by its more vigorous growth, smaller size, earlier and more abundant branching, earlier, more abundant, year-round natural flowering, less green coloration on spathe, smaller and slightly lighter colored leaf blades.

'S9' is further distinguished from 'Petite' by its more spreading growth habit and closer proximity of the inflorescences to the foliage.

'S9' further distinguished from 'Bond A' by its more upright growth habit.

Comparison between Spathiphylium 'S9' and Spathiphylium 'Petite'

| | 'S9' | 'Petite' |
|---|---|---|
| Number of lateral shoots 7.5 months from planting tissue cultured microcuttings | 6–7 | 4–5 |
| Number of open spathes 10 months from planting tissue cultured microcuttings | 2–3 | 0 |
| First flower bud emergence above foliage (Months from planting tissue cultured microcuttings) | 7 | 11 |

I claim:

1. A new and distinct cultivar of Spathiphyllum plant named 'S9', substantially as described and illustrated herein, characterized particularly as to novelty by its small size, compact growth habit, vigorous growth, early and abundant branching, exceptionally early, abundant and year-round natural flowering, good quality inflorescence from the onset of flowering, very little green coloration on spathes, good proportion between inflorescence and foliage in 10–15 cm pots, symmetrical growth habit at close pot spacing and having no unusual susceptibility to the traditional *Spathiphyllum* diseases and insects.

* * * * *